United States Patent [19]

Moment et al.

[11] Patent Number: 5,128,016
[45] Date of Patent: Jul. 7, 1992

[54] PRECIOUS METAL ANALYZER APPARATUS

[76] Inventors: Norman J. Moment, 4052 NW. 88th Ave., Unit 1D, Sunrise, Fla. 33351; Oris L. Nelson, 2101 Lawson Blvd., Apt. C-3, Delray Beach, Fla. 33445

[21] Appl. No.: 804,006

[22] Filed: Dec. 9, 1991

Related U.S. Application Data

[63] Continuation-in-part of Ser. No. 639,550, Jan. 10, 1991, Pat. No. 5,080,766.

[51] Int. Cl.$^5$ ............................................. G01N 27/26
[52] U.S. Cl. .................................. 204/406; 204/416; 204/400; 204/434; 204/153.1
[58] Field of Search ................ 204/406, 416, 153.1, 204/400, 434

[56] References Cited

U.S. PATENT DOCUMENTS 4,799,999  1/1989  Medvinsky et al. ............... 204/406

Primary Examiner—John Niebling
Assistant Examiner—Bruce F. Bell
Attorney, Agent, or Firm—Alvin S. Blum

[57] ABSTRACT

An apparatus and method for directly indicating the gold content of a metal object employs a receptacle or cell into which is deposited a small portion of an electrolyte solution. The solution preferably contains copper and iron ions, acetic acid and hydrogen peroxide. At the bottom of the cell is a first electrode preferably of pure gold in contact with the solution. The first electrode is electrically connected to an electronic measuring and indicating apparatus. The metal object to be tested is connected by a metal spring clip to the electronic apparatus and then a portion of the object is immersed in the solution so that it forms the second electrode of an electrochemical cell. The electronic apparatus measures the voltage generated in the electrochemical cell after the voltage has stabilized and indicates by indicating apparatus the gold content of the metal object.

7 Claims, 2 Drawing Sheets

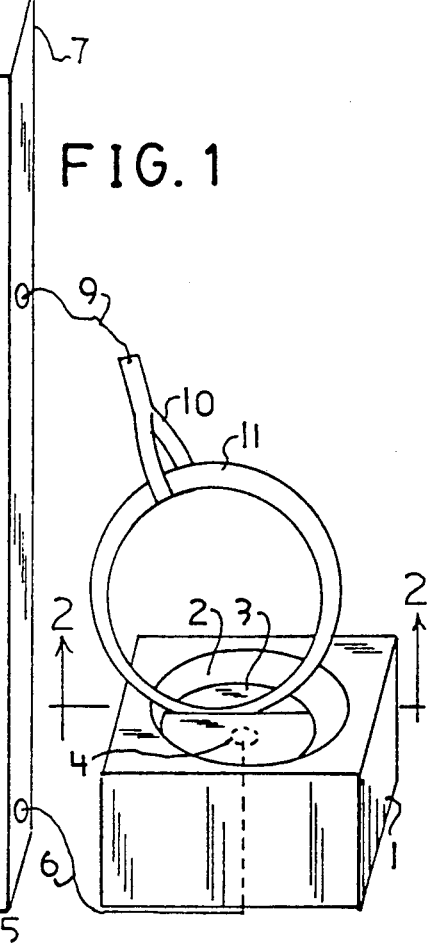
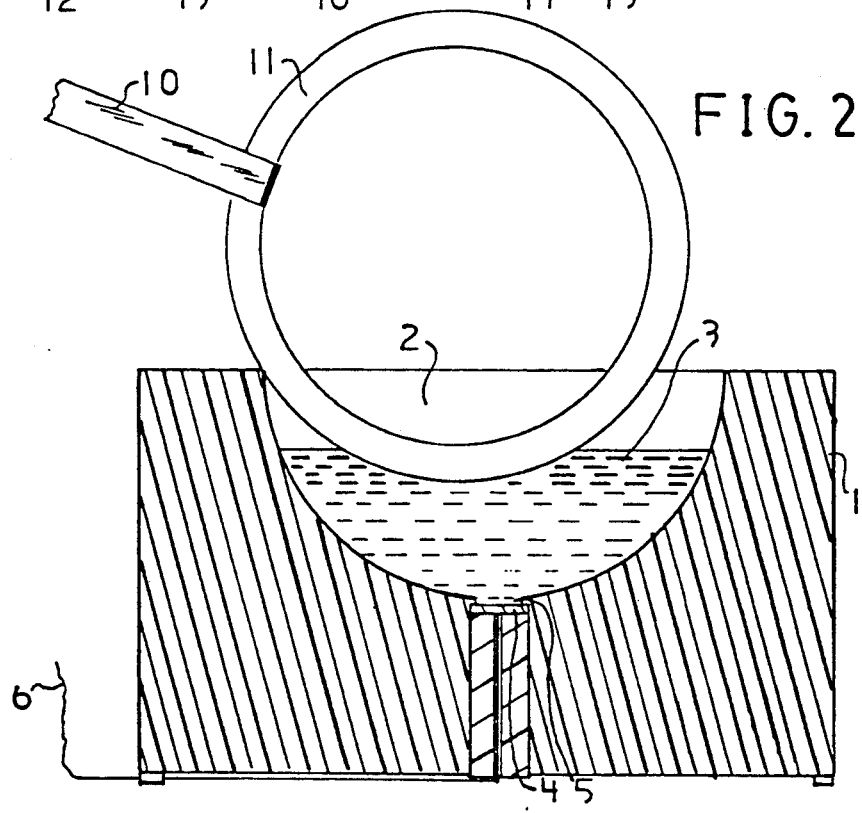
FIG. 1
FIG. 2

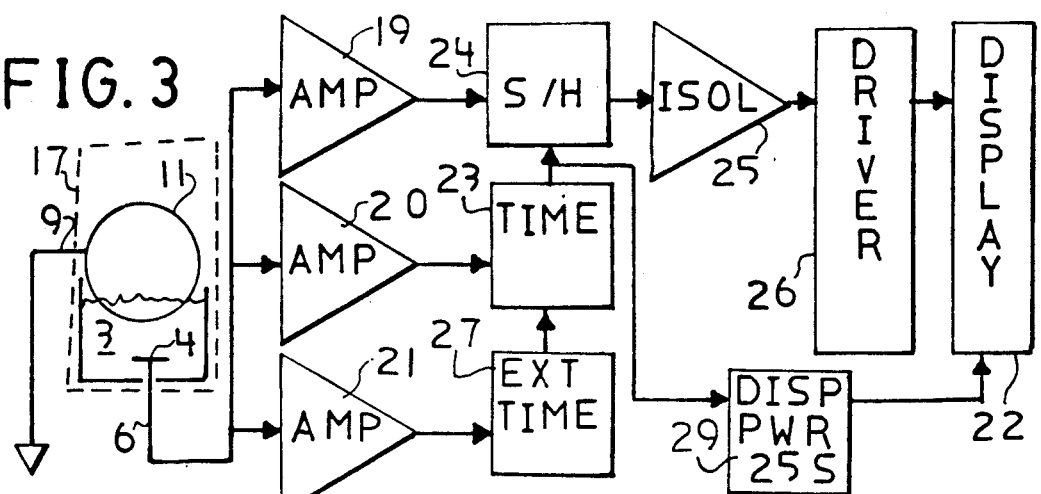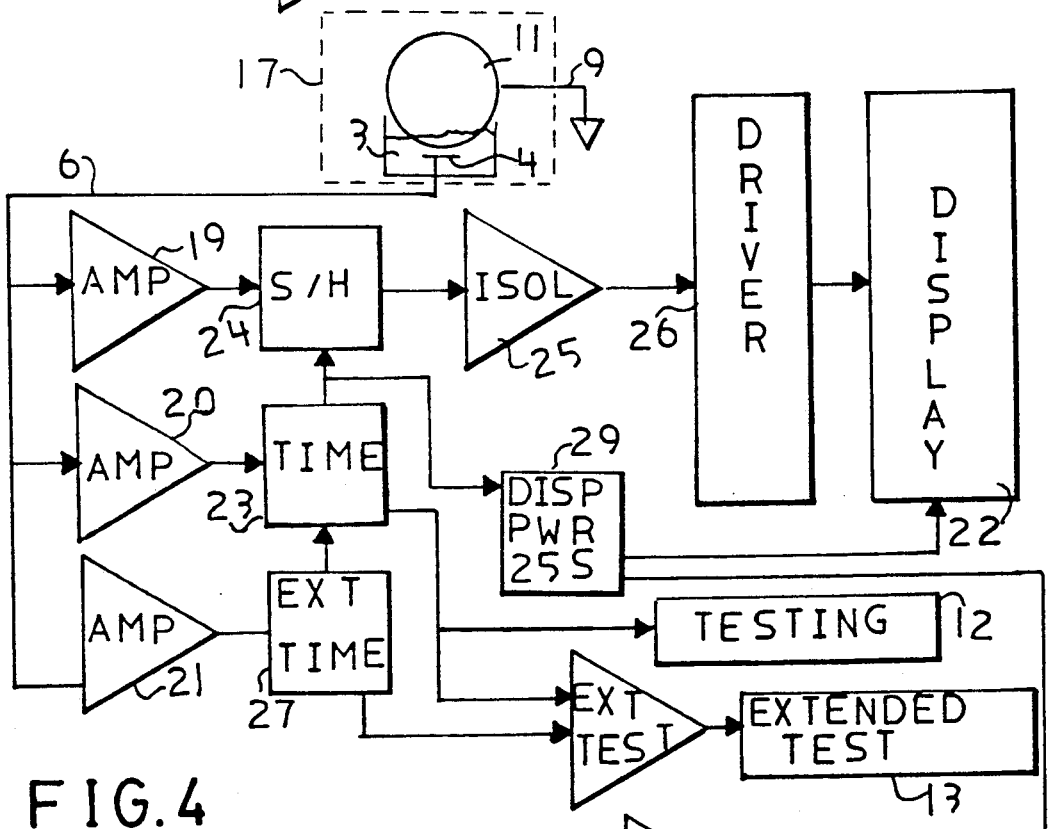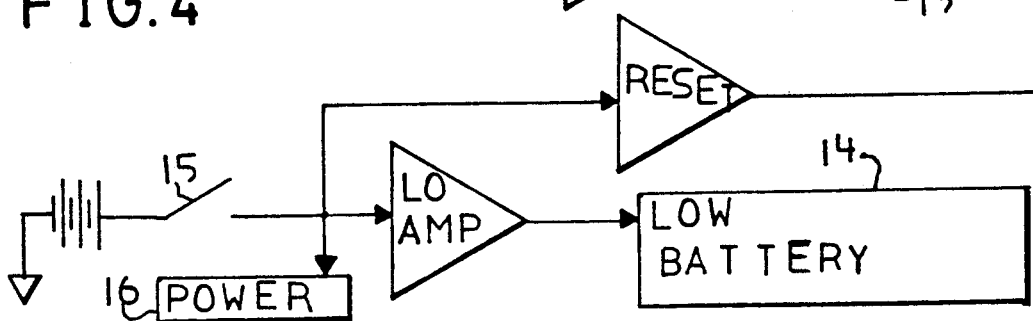

PRECIOUS METAL ANALYZER APPARATUS

This is a continuation-in-part of application Ser. No. 07/639,550, filed Jan. 10, 1991, now U.S. Pat. No. 5,080,766.

BACKGROUND OF THE INVENTION

This invention relates to systems for measuring the composition of metal alloys and more particularly to an automatic, direct-reading instrument for non-destructively indicating the gold content of a metal object.

Medvinsky et al, in U.S. Pat. No. 4,799,999 issued Jan. 24, 1989, discuss problems of assay of precious metal objects and disclose a method with direct reading of alloy composition in which the test object is first anodized and then a potential generated by the anodized surface is observed as it decays. The potential decay information is compared with empircial data and, by interpolation, the approximate karat quality of the alloy is determined and indicated on a display.

The assay methods of the prior art that accurately indicate gold content over a broad range of composition require both time and skill. The direct reading devices that are fast and easy to operate fail to indicate precise gold content and distinguish between different precious metals.

SUMMARY OF THE INVENTION

It is accordingly an object of the invention to provide a direct reading, automatic, non-destructive apparatus and method for accurately indicating the precious metal content of a metal object.

It is another object that the device and method read out in precise terms the gold content of the object under test.

It is yet another object that the device and method be easily used without requiring special skills of the operator.

The apparatus of the invention comprises a means for conveniently forming an electrochemical cell in which a pure gold electrode serves as a reference electrode in an electrochemical cell with the test metal as the second electrode. A special electrolyte wets both electrodes simultaneously and completes the circuit. An electronic device connected to the two electrodes measures electromotive force generated in the cell and indicates composition as karate of the gold alloy directly on a series of light emitting diodes (LEDS) arranged in a bar graph type of display. The reference electrode is wired to the electronic indicating apparatus and it is embedded in a slot or recess in a receptacle that holds the special electrolyte. A second wire from the electronic apparatus is connected to a metal spring clip that is clipped to the metal object to be tested. The test object is then touched to the electrolyte solution that is in contact with the reference electrode so that a circuit is completed.

The test process then begins automatically by starting a preset time interval, after which the voltage generated by the cell is measured and transformed into a direct display of the karat value of the gold on the LEDS. The prepare for the next test, the electrolyte is replaced by fresh solution and a new test object is connected to the test clip. Because only a small volume of the test object need be in contact with the electrolyte, only a small quantity of electrolyte solution is used for each test. As long as the test object does not contact the reference electrode, it need not be cleaned between tests. That is why it is recessed in the test receptacle. The test object is prepared for testing by surface cleaning. This is easily accomplished with an ink eraser. The test is completed within ten seconds and does not affect the test object, but some surface cleaning may be required.

The electrolyte solution preferably contains metal ions such as copper and iron, a buffering agent such as acetate and an oxidizing agent such as hydrogen peroxide or nitric acid.

These and other features, objects and advantages of the invention will become more apparent when the detailed description is considered in conjunction with the drawings.

BRIEF DESCRIPTION OF THE DRAWINGS

FIG. 1 is a perspective view of the apparatus of the invention.

FIG. 2 is a sectional view, taken on line 2—2 of FIG. 1.

FIG. 3 is a simplified block diagram of the apparatus of FIG. 1.

FIG. 4 is a detailed block diagram of the apparatus of FIG. 1.

DETAILED DESCRIPTION OF THE PREFERRED EMBODIMENTS

Referring not first to FIGS. 1 and 2, a plastic block 1 has an indentation 2 in its upper surface that forms a receptacle that holds a liquid electrolyte solution 3. A reference electrode, a pure gold disc (24 karat) 4 is positioned at the bottom of the indentation 2 in a recess 5 that is arranged so that a test object will not touch disc 4 when inserted into the electrolyte solution. A first wire 6 connects the reference electrode 4 to the electronic apparatus 7. A second wire 9 connects the electronic apparatus 7 to a conductive metal spring clip 10 of the type well known in the electronic art. This clip 10 is clipped onto gold object 11 to be tested for its purity and the object is inserted into indentation 2 until it touches the electrolyte solution 3. When this contact is made, a voltage is generated between the wires 6 and 9 and the electronic apparatus 7 in the electrical circuit is activated. Testing light 12 goes on as the testing cycle begins. If the gold object is sixteen karat or greater of yellow gold, the extended test light 13 goes on. Before ten seconds have passed, the LEDS 22 light up from the bottom up to the level corresponding to the karat or gold content of the test object. After a twenty-five second interval, the LEDS 22 go off and the system resets for another test. A low battery indicator 14 is provided. A power switch 15 and power on light 16 are also provided. The electrolyte is replaced with fresh solution and the system is ready for another test.

Referring now to FIGS. 3 and 4, it is seen that the reference electrode 4 and test object 11 serve as electrodes in an electrochemical cell 17 with the electrolyte solution 3 in contact with both electrodes. The voltage generated across the cell is applied to three high input impedance amplifiers 19, 20 and 21. When a voltage appears at the output of amplifier 20, it starts a timer 23. This illuminates testing light 12. A sample-and-hold circuit 24, of the type well known in the art, follows the output of amplifier 19. Timer 23; at the end of a time interval of five seconds, sends a signal to sample and hold circuit 24 which holds the voltage output from amplifier 19 at the moment. This voltage is processed by isolation amplifier 25 and display circuitry 26 of a type well known in the art to drive LEDS 22 in bar graph display. When the test object is equal to or greater than sixteen karats, the voltage out of amplifier 21 will be below a preset threshold. This condition, through extended test circuit 27 lights up extended light 13 and causes timer 23 to send a signal to the sample and hold circuit 24 at nine seconds instead of five seconds. The lower output voltage from the electrochemical cell generated by higher purity gold takes longer to stabilize, and this extension of testing time ensures accurate testing at these purity levels.

Timer display power circuit 29 maintains LEDS 22 on for twenty-five seconds to provide for reading the karat value of the test object. Then the system resets and is ready for testing a new object after replacing the electrolyte solution 3.

Other means of voltage output measurement and display well known in the art may be used such as digital readout and microprocessor operations, however this analog processing is preferred for its simplicity.

THE ELECTROLYTE COMPOSITION

The following examples are provided of preferred electrolyte solution preparation and composition:

EXAMPLE I 17 milliliters Ferric Chloride Solution, specific gravity 1.42
4.5 milliliters Glacial Acetic Acid
8.25 milliliters Nitric Acid (68%)
0.17 gram Copper (foil)
5.5 milliliters Ethylene Glycol Monoethyl Ether Acetate Heat to between 140 degrees and 150 degrees Fahrenheit until Copper is dissolved.

Bring solution to a temperature of 165 degrees to 175 degrees Fahrenheit.

Increase temperature slowly until boiling begins, at which point remove from heat immediately.

Age at room temperature for one week to stabilize.

EXAMPLE II 45 milliliters (ml) Ferric Chloride Solution (38%)
0.35 gram Copper dissolved in the Ferric Chloride solution
9 ml Glacial Acetic Acid
16.5 ml Nitric Acid (65%)
12 ml Formaldehyde (37%) added slowly and carefully.

EXAMPLE III 35 ml of the solution of Example II in a 50 ml beaker
two carbon rods ¼ inch diameter, separated by ¼ inch immersed in solution.
Pass ½ ampere of direct current for 21 minutes then
Pass 1 ampere of direct current for 3 minutes.
The resulting solution is part A
Hydrogen peroxide (15%) is part B
Mix 10 drops part A with 1 drop part B to provide enough electrolyte for a single test.

This example has a long shelf life because oxidizing agent is added just before measurement.

The metal ions in the electrolyte solution may include, copper, zinc, antimony, chromium, manganese, iron, indium, nickel, tin and cadmium. Oxidizing agents may include nitric acid, sulfuric acid, peroxides and chlorates. Stabilizing agents may include acetic, citric, formic, toluenesulfonic and phthalic acids, glycine, and formaldehyde. The reference electrode may be gold, platinum or carbon.

THE ELECTRONIC APPARATUS

It has been discovered that a voltage pulse appears between the electrodes at the moment the test object is immersed in the electrolyte. This voltage pulse may be used to begin the preset time interval.

The timer 23 and extended time circuit 27 are provided to prevent measurement before the voltage has stabilized. The instrument may be simplified by a timer that always waits nine seconds before measurement, but this prolongs some measurements needlessly. Alternatively, these circuits may be replaced by a circuit that begins measurement when the voltage has stabilized to a certain extent, such as to less than 21% per second, for example.

As best seen in FIG. 1, the instrument reads out the gold content of different alloys of gold; yellow 31; white 32; red 33; and green 34 by simply looking at the appropriate column beside the bar graph LEDS 22.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention within the scope of the appended claims.

We claim:

1. Apparatus for measuring the gold content of a metal object to be tested comprising:
   A) an electronic measuring and indicating apparatus;
   B) a receptacle means for holding a solution therein;
   C) a first electrode arranged within said receptacle means so as to be wetted by said solution, said first electrode electrically connected to said electronic measuring and indicating apparatus;
   D) electrical connecting means for electrically connecting said metal object to said electronic apparatus;
   E) electrolyte solution for insertion into said receptacle means, whereby an electrochemical cell is formed between said first electrode and a metal surface of said metal object to be tested serving as a second electrode when at least a portion of said object is immersed in said solution in said receptacle means, said electrolyte solution including metal ions selected from the group of metals consisting of iron, copper, nickel, cobalt, tin, indium, zinc, antimony, chromium, manganese and cadmium; and
   F) said electronic measuring and indicating apparatus including measuring means for measuring the electrochemical voltage generated between said first and second electrodes in said electrochemical cell without the prior application of an external voltage; delay means for delaying said measuring until said electrochemical voltage has substantially stabilized; and indicating means for displaying to an operator the gold content of said metal object based upon said electrochemical voltage.

2. The apparatus according to claim 1, in which said first electrode is comprised of an element selected from the group of elements consisting of gold, platinum and carbon.

3. The apparatus according to claim 1, in which said first electrode is arranged to be wetted by said electrolyte solution while being protected from contact by said second electrode.

4. The apparatus according to claim 1, in which said electrolyte solution comprises: iron and copper ions; nitric and acetic acids, formaldehyde and hydrogen peroxide.

5. The apparatus according to claim 4, in which said electrolyte solution is treated by passage of an electric current therethrough prior to addition of said hydrogen peroxide.

6. The apparatus according to claim 1, in which said electrolyte solution includes: oxidizing agents selected from the group consisting of nitric acid, sulfuric acid, peroxides and chlorates; and stabilizing agents from the group consisting of citric, acetic, formic, toluene sulfonic and phthalic acids, glycine, mono or polyhydroxl aliphamic compounds and derivatives thereof, and formaldehyde.

7. The apparatus according to claim 1, in which said electrolyte solution includes copper and iron ions, acetic acid, nitric acid and ethylene glycol monoethyle ether acetate.

* * * * *